United States Patent
Sinderby

(12) 
(10) Patent No.: US 6,584,347 B1
(45) Date of Patent: Jun. 24, 2003

(54) DISTURBANCE-FREE ELECTROMYOGRAPHIC PROBE

(75) Inventor: Christer Sinderby, Montreal (CA)

(73) Assignee: Universite de Montreal, Montreal (CA)

( * ) Notice: Subject to any disclaimer, the term of this patent is extended or adjusted under 35 U.S.C. 154(b) by 0 days.

(21) Appl. No.: 09/744,039

(22) PCT Filed: Jul. 16, 1999

(86) PCT No.: PCT/CA99/00652

§ 371 (c)(1), (2), (4) Date: May 25, 2001

(87) PCT Pub. No.: WO00/03637

PCT Pub. Date: Jan. 27, 2000

(30) Foreign Application Priority Data

Jul. 16, 1998 (CA) ............................................. 2243382

(51) Int. Cl.[7] ................................................. A61B 5/04
(52) U.S. Cl. ..................... 600/546; 600/372; 600/373; 600/374; 606/41; 606/45
(58) Field of Search ............. 606/41, 45; 600/372–374, 600/546

(56) References Cited

U.S. PATENT DOCUMENTS

| | | | |
|---|---|---|---|
| 4,582,064 A | 4/1986 | Sorger | ........................ 128/635 |
| 5,230,786 A | 7/1993 | Preidel | ....................... 204/435 |
| 6,015,407 A | * 1/2000 | Rieb et al. | ..................... 606/41 |
| 6,185,465 B1 | * 2/2001 | Mo et al. | ..................... 607/138 |
| 6,216,704 B1 | * 4/2001 | Ingle et al. | ................. 128/898 |

OTHER PUBLICATIONS

Kingma, Y.J. et al., "*Improved Ag/AgCI pressure electrodes*", 2200 Medical & Biological Engineering & Computing vol. 21 (1983) May No. 3 Stevenage, Herts., Great Britain XP–002118744.

* cited by examiner

*Primary Examiner*—Teresa Walberg
*Assistant Examiner*—Shawntina T. Fuqua
(74) *Attorney, Agent, or Firm*—Darby & Darby

(57) ABSTRACT

A myographic probe for detecting an electrical signal produced by a muscle and for reducing the influence of electrode disturbances. The probe includes electrodes and a disturbance reducing interface covering each electrode thereby segragating the electrodes from the muscle. Electrode disturbances include problems such as those related to the motion of the electrodes, changes in the pressure applied to the electrode, and/or intermittent contact with sourrounding tissue. The disturbance reducing interface is ion permeable and is, when dry, less conductive than the electrodes. The disturbance reducing interface may comprise a matrix of permeable material such as a mesh, foam, or other porous materials. The probe may be in the form of a catheter and be advantageously used in a human cavity such as the oesophagus. Another advantage of the invention is the possibility of using electrodes which are different from conventional wound wire electrodes.

19 Claims, 4 Drawing Sheets

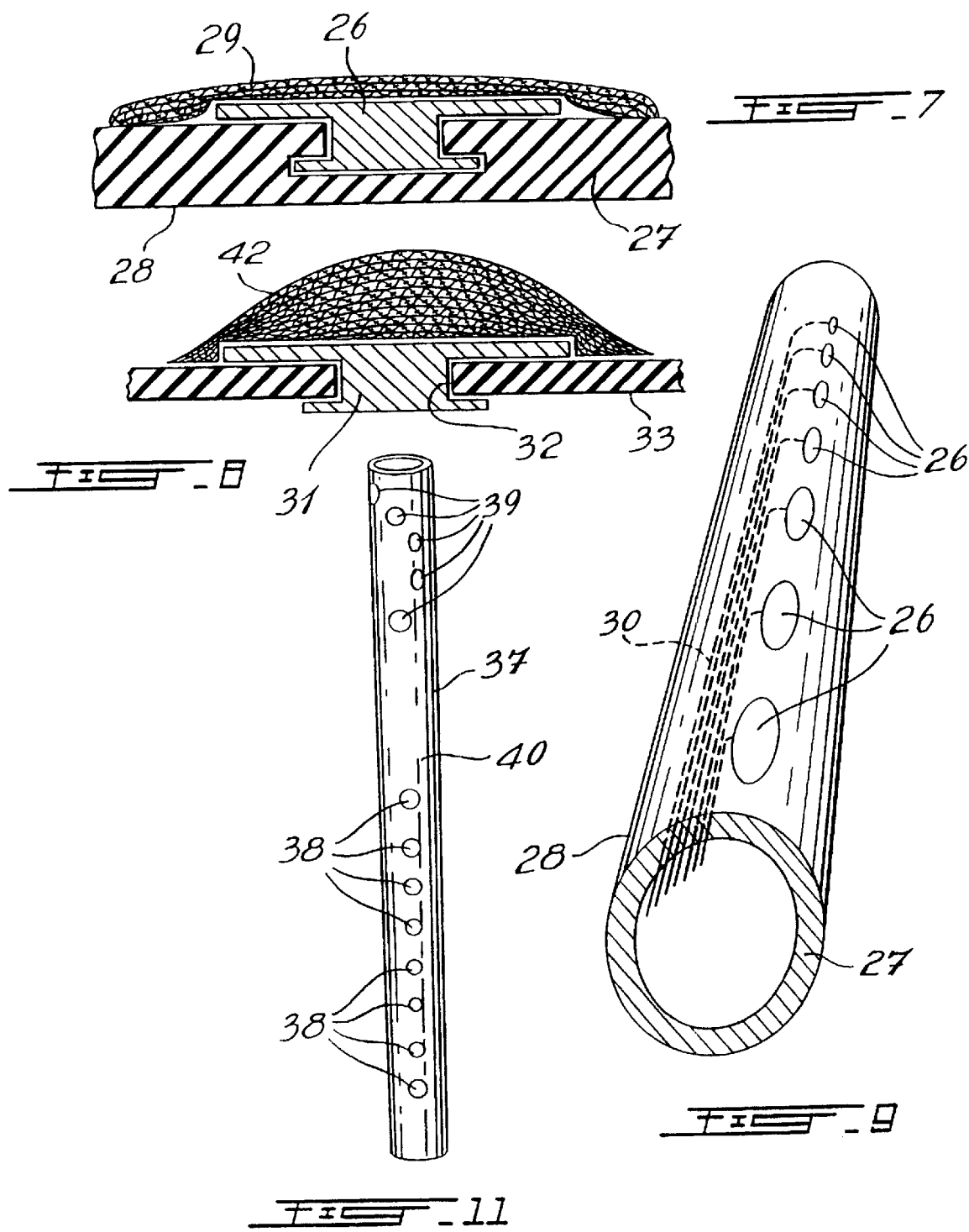

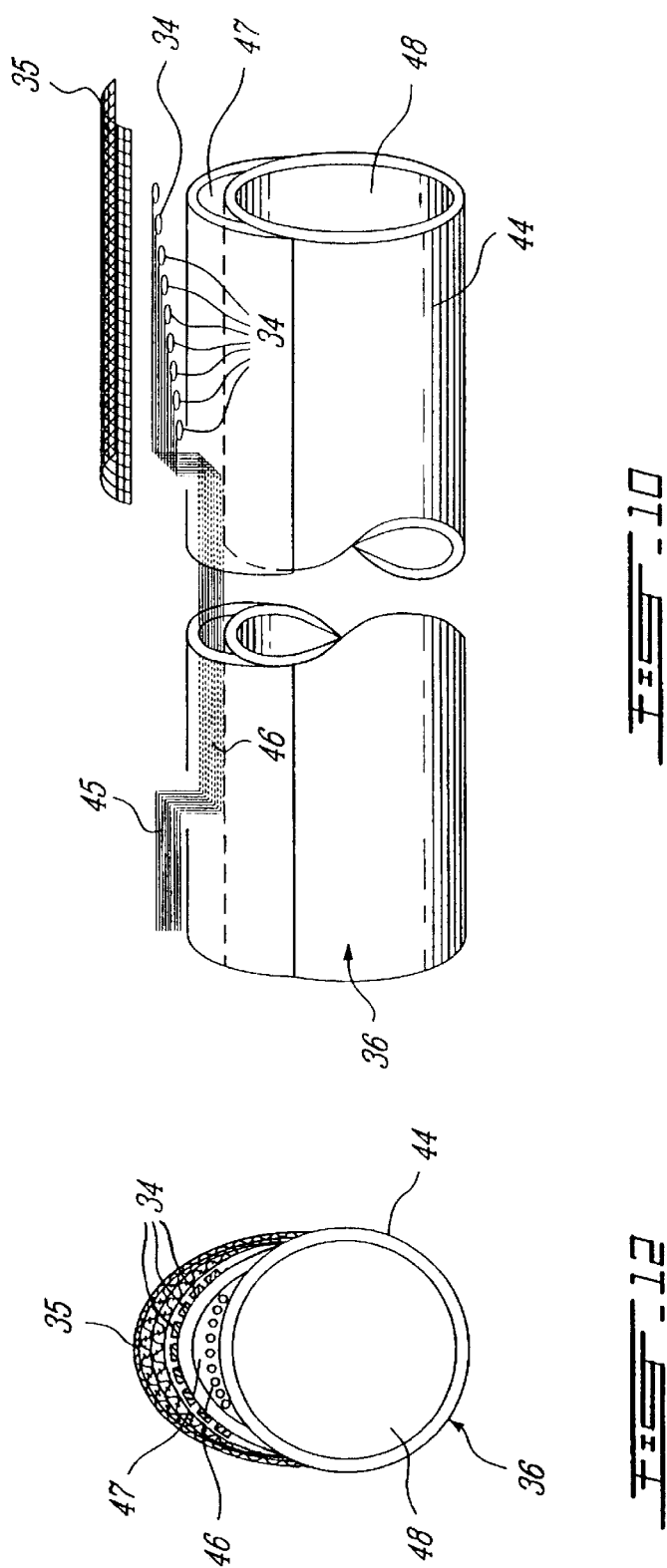

DISTURBANCE-FREE ELECTROMYOGRAPHIC PROBE

BACKGROUND OF THE INVENTION

1. Field of the Invention

The present invention relates to an apparatus for reducing disturbances induced in a signal measurement or recording, in particular, but not exclusively, by movement of the electrodes or changes in the pressure applied to the electrodes.

2. Brief Description of the Prior Art

Oesophageal recording of diaphragm electromyogram (EMG) has traditionally been problematic due to the low amplitude of the EMG signal relative to the artifactual disturbances such as, in particular, the so-called electrode motion artifacts. At high gain settings, large electrode motion artifacts lead to saturation of the output of the preamplifier, thereby causing a temporary loss of the EMG signal. This problem of the prior art makes EMG recording very difficult during dynamic manoeuvres, such as for example rapid shallow breathing or panting.

OBJECTS AND SUMMARY OF THE INVENTION

A first object of the present invention is to provide a technology capable of reducing disturbances induced in a measurement or recording by:

movements of detecting electrodes;

changes in the pressure applied to these electrodes; or other mechanical influence on the electrodes, generally referred to as motion artifacts.

Another object of the present invention is to reduce the amplitude of motion artifacts relative to the amplitude of the EMG signal to thereby reduce the possibility for saturation of the preamplifier.

A third object of the present invention is to overcome the problems of the prior art related to low signal-to-artifact ratio.

A further object of the present invention is to improve bipolar electrode measurements of diaphragm electromyogram (EMG).

In a preferred embodiment of the invention, there is provided a measurement apparatus for detecting an electrical signal produced by a muscle while reducing signal disturbances caused by motion artifacts, the measurement apparatus comprises:

a) a probe;

b) at least one electrode mounted on said probe; and c) a disturbance reducing interface attached to said probe and covering said at least one electrode, the interface being ion permeable and segregating said at least one electrode from the muscle.

The objects, advantages and other features of the present invention will become more apparent upon reading of the following non restrictive description of preferred embodiments thereof, given by way of example only with reference to the accompanying drawings.

BRIEF DESCRIPTION OF THE DRAWINGS

In the appended drawings:

FIG. 7 is a longitudinal, partial cross sectional view of the free end section of an oesophageal catheter, showing an electrode embedded in the material of the catheter, and a matrix of permeable material applied to the embedded electrode;

FIG. 8 is a longitudinal, partial cross sectional view of the free end section of an oesophageal catheter, showing a stud electrode and a matrix of permeable material applied to the stud electrode;

FIG. 9 is a partial perspective view of the free end section of the oesophageal catheter of FIG. 7, showing an array of electrodes such as shown in FIG. 7, embedded into the material of the catheter;

FIG. 10 is a partial perspective view of the free end; section of an oesophageal catheter, showing an array of button electrodes covered by a matrix of permeable material applied to the outer surface of the oesophageal catheter;

FIG. 11 is a partial perspective view of the free end section of an oesophageal catheter, showing an array of button electrodes as well as an array of grounding electrodes; and FIG. 12 is an end cross sectional view of the array of button electrodes of FIG. 10 covered by the matrix applied to the outer surface of the oesophageal catheter.

DETAILED DESCRIPTION OF THE PREFERRED EMBODIMENTS

The present invention relates to a technology capable of reducing disturbances induced in an electrical signal measurement and/or recording by movement of detecting electrodes or changes in the pressure applied to these electrodes. The electrodes are conductive elements used to detect electrical activity. The range of applications of the present invention includes electrical signal measurement and/or recording wherein electrodes are immersed in an eleclectrolyte (so-called wet electrodes). A typical example is the measurement and/or recording of diaphragm electromyogram (EMG), oesophageal peristalsis, or ECG with electrodes positioned on a catheter which in turn is introduced in the oesophagus.

Although the preferred embodiments will be described hereinafter with reference to oesophageal catheters and an application to the measurement of diaphragm electromyogram (EMG), it should be kept in mind that it is within the scope of the present invention to envisage other applications for this technology using other types of catheters or probes.

Figure 1:
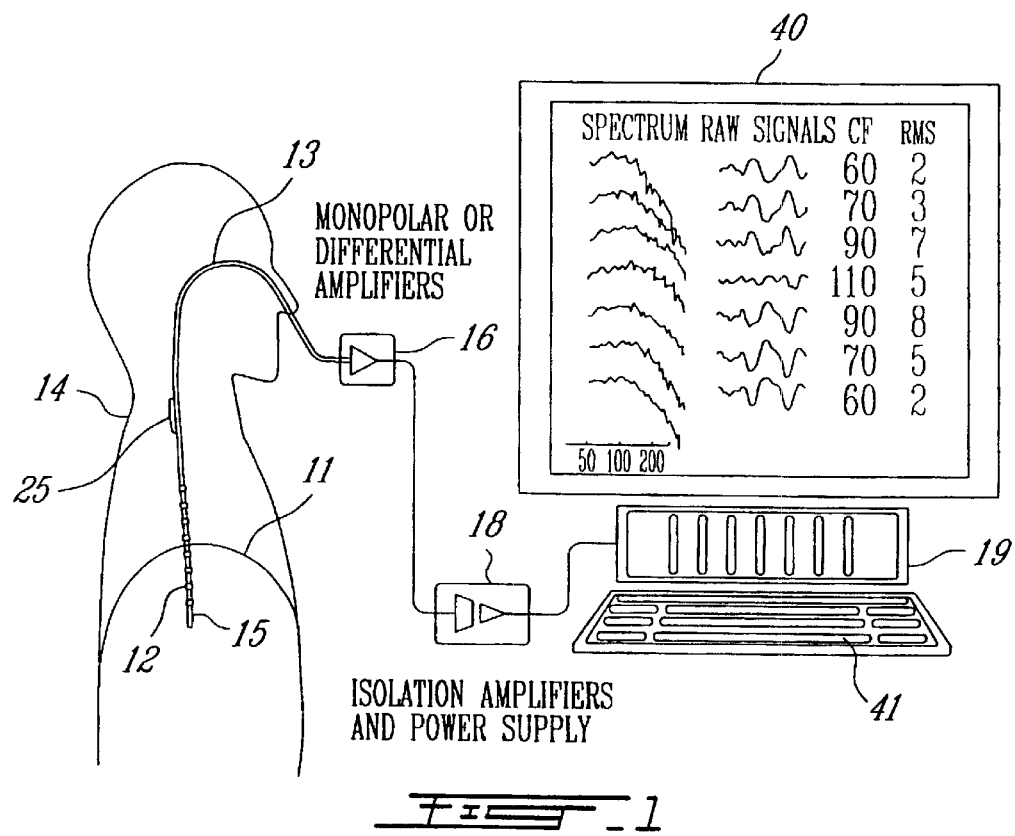
FIG. 1 is a schematic representation of a set-up of an EMG analysis system.
Figure 2:
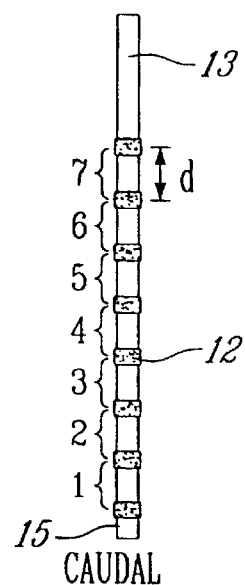
FIG. 2 is a side elevation view of the free end section of an oesophageal catheter on which an array of electrodes of the EMG analysis system of FIG. 1 is mounted.
Figure 3:
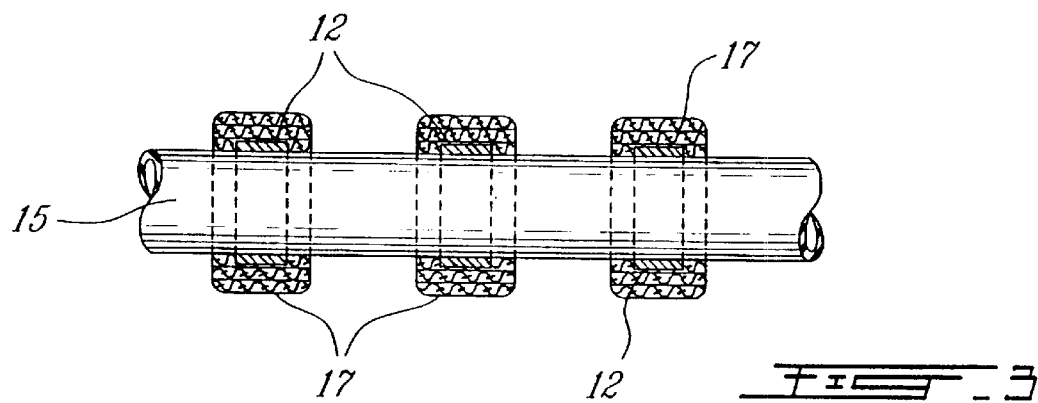
FIG. 3 is a longitudinal, partial cross sectional view of the free end section of the oesophageal catheter of FIG. 2, showing an individual matrix of permeable material applied to each separate electrode of the array.
Figure 4:
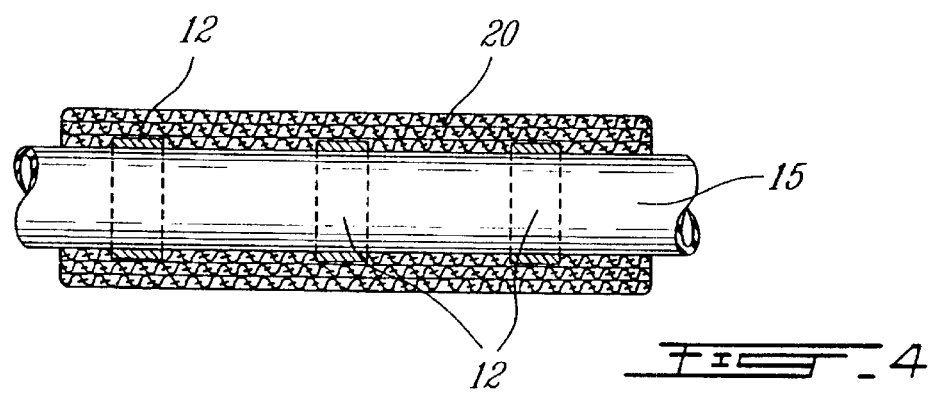
FIG. 4 is a longitudinal, partial cross sectional view of the free end section of the oesophageal catheter of FIG. 2, showing a continuous matrix of permeable material applied to and spanning the entire electrode array.

Referring to FIGS. 1 and 2, to measure EMG activity of the diaphragm 11 of a human patient 14, an array of electrodes such as 12 are mounted on the free end section 15 of an oesophageal catheter 13, with an inter-electrode distance d (FIG. 2). The distance d is adjusted in relation to body size; distance d will be larger for an adult than for an infant. The catheter 13 is a hollow tube having a diameter related to body size; the diameter will be smaller for infants than for adults. The catheter diameter, electrode size as well as the inter-electrode distance d may also vary in relation to the purpose of the catheter use.

As shown in FIG. 1, the catheter 13 is introduced into the patient's oesophagus through one nostril or the mouth until the array of electrodes 12 is situated at the level of the gastro-oesophageal junction. Of course, positioning of the electrode array comprising a series of differentially and axially arranged electrode pairs (for example electrode, pairs 1–7 of FIG. 2) is guided by the electrocardiographic (ECG) recordings and the diaphragm EMG. Alternatively, the electrodes 12 are monopolar electrodes differentiated in a computer, for example computer 19 of FIG. 1. When required, ground is obtained through a separate, grounding electrode structure 25 (FIG. 1).

Positioning of an electrode at the oesophageal hiatus (where the oesophagus passes through the diaphragm is guided by visual inspection and/or computer algorithms studying the intensity, shape and polarity of ECG and diaphragm EMG signals. When the electrode is close to the oesophageal hiatus, i.e. next to the heart, ECG signal amplitude is high. If the electrode array is positioned close to the mouth (away from the heart), ECG signals present lower amplitudes at the proximate electrodes, and higher amplitudes at the distal electrodes. If the electrode array is positioned too far in the stomach, ECG has a high amplitude at the proximate electrodes of the array and a low amplitude at the distal electrodes. If the electrode array spans the region of the heart, ECG signals will show a time shift along the electrode array. If the electrodes are positioned away from the heart, ECG signals show no time lag. Diaphragm EMG signals obtained through electrode pairs located above and below the diaphragm have opposite polarities (with no time shift). EMG signals obtained on the same side of the diaphragm show the same polarity (and no time shift). The characteristics described in this paragraph will help the operator to adequately position the array of electrodes.

Figures 5, 6:
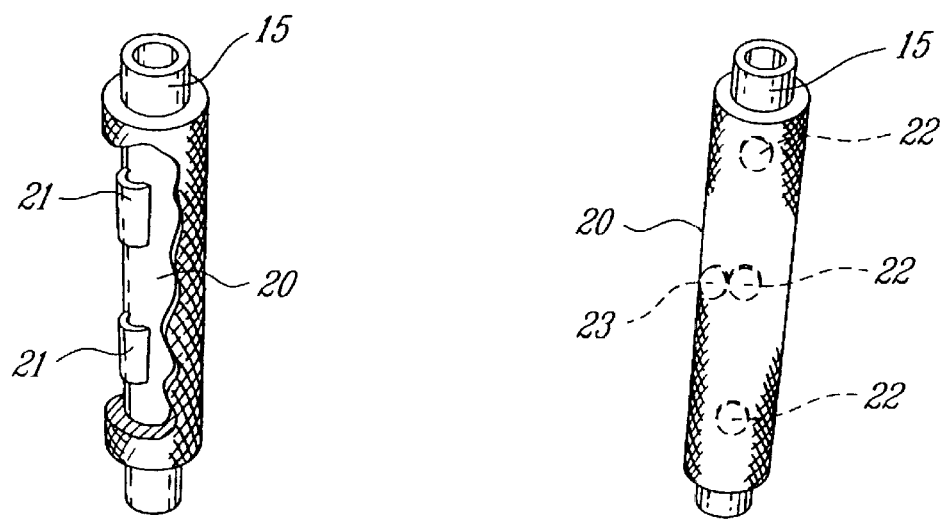
FIG. 5 is a partial perspective view of the free end section of an oesophagpal catheter, showing an array of semicircular electrodes and a continuous matrix of permeable material applied to and spanning the entire array of semicircular electrodes.
FIG. 6 is a partial perspective view of the free end section of an oesophageal catheter, showing an array of button electrodes which can be circular, square, rectangular, or of any other shape, and a continuous matrix of permeable material applied to and spanning the entire array of button electrodes.

According to a preferred embodiment, an electrode 12 is mounted on the free end section 15 of the catheter 13 by winding stainless steel wire (not shown) around catheter 13. The wound stainless steel wire presents a rough surface smoothed out by solder, which in turn is electroplated with nickel, copper and then gold or silver. Use of other metallic elements such as semicylindrical electrodes 21 (FIG. 5), button electrodes 22 and 23 (FIG. 6), etc., could be contemplated. The button electrodes can be arranged into a longitudinal linear array (electrodes 22), or at least one button electrode (see 23) can be angularly offset from the electrodes 22 about the longitudinal axis of the catheter section 15.

For larger diameter feeding tubes or catheters, electrodes such as electrode 26 in FIG. 7 can be embedded into the material 27 of the feeding tube or catheter 28. FIG. 9 shows a longitudinal array of electrodes 26 embedded into the material 27 of the free end section of the oesophageal catheter 28. FIG. 9 also shows the electric wires such as 30, embedded in the material 27 of the catheter 28, and individually connecting each electrode 26 to the amplifiers 16 of FIG. 1. In the example of FIGS. 7 and 9, the electrodes 26 are oval. The electric wires such as 30 in FIG. 9 individually connect each electrode such as 26 with a respective input of the monopolar or differential (depending on the monopolar or differential arrangement of the electrodes 12 or 26) amplifiers 16 (FIG. 1). Obviously, these electric wires 30 follow the catheter such as 28 from the respective electrodes such as 26 to the corresponding amplifiers 16; the electric wires 30 can be embedded in the material such as 27 of the catheter such as 28 or passed separately outside (see for example 45 in FIG. 10) or inside (see for example 46 in FIG. 10) the catheter lumen 47 depending on the intended application. The electric wires such as 30 transmitting the EMG signals collected by the various electrodes such as 26 are necessarily electrically insulated from each other and preferably surrounded by a conductive mesh constituting a shield against external disturbances.

Referring now to FIG. 8, a stud electrode 31 is illustrated. Each stud electrode 31 is mounted in a hole 32 made through the wall of an oesophageal catheter 33.

The electrodes such as 34 in FIG. 10 can also be applied by means of glue or any other suitable adhesive material or compound, including double adhesive tape.

In the example of FIGS. 10 and 12, a linear array of oval electrodes 34 is mounted on the outer surface 44 of a catheter 36 comprising two longitudinal lumens 47 and 48. Referring to FIG. 12, each electrode 34 is applied to the catheter surface 44. As described in the foregoing description, the electric wires (see 45 and 46) for individually connecting the electrodes 34 to the amplifiers 16 will extend either inside lumen 47 (see 46 in FIG. 10), inside lumen 48, outside the catheter 36 (see 45 in FIG. 10), or embedded in the material of the catheter 36.

FIG. 11 is a partial perspective view the free end section of an oesophageal catheter 37, comprising a longitudinal, linear array of button electrodes 38. FIG. 11 also shows an example of grounding electrode structure (see 25 in FIG. 1). In the example of FIG. 11, the grounding electrode structure comprises a helical array of grounding electrodes 39 mounted on the outer surface 40 of the catheter 37. Of course, the array of grounding electrodes 39 is centered on the longitudinal axis of the catheter 37 and presents the general configuration of a cylindrical helix.

Pressure sensors, pH sensors, thermistors and other detector devices can be added onto the catheter in accordance with the requirements of the intended application.

Referring back to FIG. 1, the group of amplifiers 16 amplifies and band-pass filters each EMG signal. The amplified EMG signals are sampled by a personal computer 19 through respective isolation amplifiers of a unit 18, to form signal segments of fixed duration. Unit 18 supplies electric power to the various electronic components of the amplifiers 16 and isolation amplifiers while ensuring adequate isolation of the patient's body from such power supply. The unit 18 also incorporates bandpass filters included in the respective EMG signal channels to eliminate the effects of aliasing. The successive EMG signal segments are then digitally processed into the personal computer 19 after analog-to-digital conversion thereof. This analog-to-digital conversion is conveniently carried out by an analog-to-digital converter implemented in the personal computer 19. The personal computer 19 includes a monitor 40 and a keyboard 41.

It is believed to be within the capacity of those of ordinary skill in the art to construct suitable amplifiers 16 and an adequate isolation amplifiers and power supply unit 18. Accordingly, the amplifiers 16 and the unit 18 will not be further described in the present specification.

To eliminate the problems related to motion of the electrode, changes in the pressure applied to the electrode, and/or intermittent contact with surrounding tissue, a motion artifact reducing interface is applied to the electrode surface. The problems listed above can grouped as disturbances; the motion artifact reducing interface may therefore also be referred to as a disturbance reducing interface. The motion artifact reducing interface advantageously consists of a matrix of permeable material comprising, for example, a mesh, foam or other porous material, e.g. a fine filament matrix of nylon. The principle of operation is that the matrix of permeable material creates an interface that hosts ions and electrodes and prevents direct contact between the metal surface of the electrode and the surrounding body tissue. The type of permeable material and thickness thereof is not crucial for performance as long as it forms an ion saturated interface producing no direct contact between the electrode and body tissue. However, excessive thickness may cause increased distance between the electrode and muscle, which will weaken the signal strength and lower the frequency content of this signal.

As illustrated in FIGS. 3–8 and 10, the matrix of permeable material is applied to the exposed surface of the electrodes where the ion concentration gradients are largest to reduce mechanically-caused movements of ions.

The matrix can be formed by separate single matrices 17 (FIG. 3), 29 (FIG. 7) or 42 (FIG. 8) individually applied to or integrated in the exposed surface of each electrode 12 (FIG. 3), 26 (FIG. 7) or 31 (FIG. 8). For example, each individual matrix 17, 29 or 42 can be glued on, or adhere to by other means, the outer surface of the catheter to cover the associated electrode. However no adhesive material may cover the electrode surface.

The matrix can also take the form of a continuous matrix 20 (FIGS. 4, 5 and 6) or 35 (FIGS. 10 and 12). For example, the continuous matrix may form a tube that can be pulled over the catheter to cover the entire span of the array of electrodes 12 (FIG. 4), 21 (FIG. 5), 22 and 23 (FIG. 6), and 34 (FIGS. 10 and 12). In the case of a continuous matrix spanning the entire electrode array, the conductivity of the material constituting the matrix, when dry, has to present a conductivity lower than the conductivity of the metal forming the electrodes, whereby electrical conduction is carried out across the matrix, i.e., through the electrolyte. These matrices provide a much more stable voltage with a reduction of the so-called electrode motion induced artifacts on the diaphragm EMG signal.

Also, the matrix can either cover the entire circumference of the catheter (see matrices 20 and 17 of FIGS. 3–6) or a portion of the circumference of the catheter (see matrices 29, 42 and 35 of FIGS. 7, 8, 10 and 12). Again these matrices can be adhered to the outer surface of the catheter to cover the electrodes; no adhesive material may cover the electrode surface.

Other alternatives (not shown) are (a) to wind or wrap the matrix around the catheter and the electrodes, and (b) to host or embed the electrodes into the matrix.

The electrode structure according to the invention can be applied to measurement of the diaphragm electromyogram (EMG) exclusively or in combination with a device for providing feeding/medication/liquid supply to the patient, and emptying of gastric liquids, common to the treatment of patients in need of ventilatory support. The electrode structure is usable to provide diaphragm EMG signals from a plurality of conductive elements which in turn can be used to:

monitor diaphragm EMG (frequency, amplitude or power);

trigger and control gas flow, gas volume or gas pressure delivered by a mechanical lung ventilator; and control a closed loop ventilator system that will automatically adjust the level of inspiratory support in proportion to changes in the neuro-ventilatory efficiency such that the neural drive remains stable at a desired target level.

The closed loop ventilator system control can further use the intensity of the diaphragm electromyogram (EMG) obtained immediately before inspiratory flow occurs to quantify pre-inspiratory breathing efforts.

The catheter including the array of electrodes is aimed to be disposed of after a single use; however, when desired, conventional sterilization techniques can be applied in view of re-using the catheter. The catheter can stay in the same patient for extensive periods of time; it is therefore important that the electrodes and matrix be made out of a non-allergen material.

Retrocardiac recording of electrocardiogram and oesophageal peristalsis are other possible applications.

The electrode structure according to the invention is applicable in all patients on ventilatory support and will enhance the possibility of obtaining spontaneous breathing and of optimizing patient ventilator interaction. There exists also a utility for this electrode structure during anaesthesia for monitoring vital fonctions of the patient. The electrode structure can be used in connection with all kinds of ventilator systems in intensive care unit settings or other wards where assisted ventilation is required.

Although the present invention has been described hereinabove with reference to preferred embodiments thereof, these embodiments can be modified at will, within the scope of the appended claims, without departing from the spirit and nature of the subject invention.

What is claimed is:

1. An electrode structure comprising an electrode support and at least one pair of EMG electrodes mounted on the electrode support to sense an electrical signal produced by a muscle of a living body, wherein the electrode structure further comprises a motion-artifact-reducing interface applied to the electrodes of said pair to prevent direct contact between tissues of the living body and the electrodes, and wherein:

the motion-artifact-reducing interface comprises an electrolyte-permeable matrix having an inner surface applied to the electrodes and an outer surface for direct application to the tissues of the living body, the electrolyte-permeable matrix forming an ion-host structure propagating the electrical signal produced by the muscle toward the electrodes to thereby reduce motion artifacts; and the electrolyte-permeable matrix having a lower conductivity than the electrodes when the electrolyte-permeable matrix is dry.

2. An electrode structure as recited in claim 1, wherein the motion-artifact-reducing interface comprises individual interfaces respectively applied to the electrodes.

3. An electrode structure as recited in claim 1, wherein the motion-artifact-reducing interface comprises a single interface covering the two electrodes of the pair.

4. An electrode structure as recited in claim 1, wherein the electrolyte-permeable matrix comprises a mesh.

5. An electrode structure as recited in claim 1, wherein the electrolyte-permeable matrix comprises a foam.

6. An electrode structure as recited in claim 1, wherein the electrolyte-permeable matrix comprises porous material.

7. An electrode structure as recited in claim 1, wherein the electrolyte-permeable matrix comprises nylon filaments.

8. An electrode structure as recited in claim 1, wherein the electrode support comprises a catheter for insertion in the living body.

9. An electrode structure as recited in claim 8, wherein the catheter is an oesophageal catheter.

10. An electrode structure as recited in claim 8, wherein the electrolyte-permeable matrix covers the circumference of the catheter.

11. An electrode structure as recited in claim 1, wherein said at least one pair of electrodes comprises a plurality of pairs of EMG electrodes forming a longitudinal array of electrodes.

12. An electrode structure as recited in claim 11, wherein the array of electrodes comprises at least one electrode angularly offset from a longitudinal axis defined by the remaining electrodes of the array.

13. A method of reducing motion artifacts applied to an electrode structure comprising an electrode support, at least one pair of EMG electrodes mounted on the electrode support to sense an electrical signal produced by a muscle of a living body, said motion artifact reducing method comprising:

applying to the electrodes of said pair a motion-artifact-reducing interface comprising an electrolyte-permeable matrix having inner and outer surfaces, having, when dry, a lower electrical conductivity than the electrodes, and forming an ion-host structure, wherein applying the motion-artifact-reducing interface to the electrodes comprises applying the inner surface of the electrolyte-permeable matrix to the electrodes;

applying the outer surface of the electrolyte-permeable matrix directly to tissues of the living body; and propagating the electrical signal produced by the muscle toward the electrodes through the ion-host structure to thereby reduce motion artifacts.

14. An electrode structure as recited in claim 1, further comprising a separate grounding electrode structure.

15. An electrode structure as recited in claim 8, wherein the electrolyte-permeable matrix is an electrolyte-permeable matrix partly encircling the catheter.

16. An electrode structure as recited in claim 1, wherein the EMG electrodes comprise at least one semi-cylindrical electrode.

17. An electrode structure as recited in claim 1, wherein the EMG electrodes comprise at least one button electrode.

18. An electrode structure as recited in claim 17, wherein the bottom electrode is partly embedded in the material of the electrode support.

19. An electrode structure as recited in claim 11, wherein the electrode support is elongated and defines a longitudinal axis, and wherein the electrodes of said longitudinal array are angularly offset with respect to each other about said longitudinal axis of the electrode support.

* * * * *